United States Patent [19]
Morris

[11] Patent Number: 5,921,951
[45] Date of Patent: Jul. 13, 1999

[54] APPARATUS FOR PUMPING FLUID AT A STEADY FLOW RATE

[75] Inventor: Livingston B. Morris, Devon, Pa.

[73] Assignee: Therakos, Inc., Exton, Pa.

[21] Appl. No.: 08/974,200

[22] Filed: Nov. 19, 1997

Related U.S. Application Data

[60] Provisional application No. 60/031,651, Nov. 22, 1996.

[51] Int. Cl.$^6$ .................................................. A61M 37/00
[52] U.S. Cl. ........................ 604/6; 604/4; 604/5; 604/29; 417/98; 417/307
[58] Field of Search ................................ 604/131, 29, 28, 604/30, 65, 48, 27, 19, 7, 4, 5, 6; 424/450; 417/16, 17, 52, 92, 93, 95, 96, 97–98, 121, 122, 437, 472, 473, 474, 477, 478

[56] References Cited

U.S. PATENT DOCUMENTS

| | | | |
|---|---|---|---|
| 3,308,765 | 3/1967 | Mutschler et al. | 417/307 |
| 4,180,067 | 12/1979 | Derlien | 604/131 X |
| 5,193,545 | 3/1993 | Marsoner et al. | 604/27 X |

Primary Examiner—Wynn Wood Coggins
Assistant Examiner—N. Kent Gring
Attorney, Agent, or Firm—Andrew C. Farmer

[57] ABSTRACT

An apparatus for pumping fluid at a steady rate. A first drive chamber having a movable outer surface, and a second drive chamber having a movable outer surface are provided. The apparatus further includes a block having a plurality of internal passages including a first passage for receiving the fluid into the block and a second passage for discharging the fluid from the block at the steady rate. The block has first and second internal chambers which are in fluid connection with the first and second passages. The first internal chamber has a first flexible surface for mating with the movable outer surface of the first drive chamber, and the second internal chamber has a second flexible surface for mating with the movable outer surface of the second drive chamber. At least one actuator is provided for applying positive pressure to the first flexible surface while simultaneously applying negative pressure to the second flexible surface and for applying negative pressure to the first flexible surface while simultaneously applying positive pressure to the second flexible surface. The actuator is respectively coupled to the first and second flexible surfaces by the first and second drive chambers.

18 Claims, 6 Drawing Sheets

APPARATUS FOR PUMPING FLUID AT A STEADY FLOW RATE

This application claims the benefit of United States provisional application 60/031,651 filed on Nov. 22, 1996.

FIELD OF THE INVENTION

The present invention relates generally to systems for controlling fluid flow. More particularly, the present invention relates to systems for infusing fluids in and withdrawing fluids from patients undergoing medical care. Still more particularly, the present invention relates to systems for infusing fluids in and withdrawing fluids from medical patients at a steady flow rate.

BACKGROUND

Photopheresis is a treatment involving the separation of white cells from the blood, addition of a photoactivatable drug, and U.V. irradiation of the white cells before reinfusion to the patient. In known photopheresis systems, the blood is pumped by peristaltic roller pumps. Such roller pumps require use of complex tubing sets and have the potential to cause cell damage under high outlet pressure conditions. Alternatively, blood has also been pumped with discrete pump chambers and valves which also require complex tubing sets. Such discrete pump chambers and valves are considered to be less damaging to cells under high outlet pressures.

A very real advancement in photopheresis systems would result if the size and complexity of the associated tubing could be reduced, even at the cost of a more complex driving system, since the driving system is permanent equipment and the tubing set must be replaced after each treatment session. Such a result has been accomplished with peritoneal dialysis systems, where the flow of dialysate is controlled entirely with diaphragm pumps and valves driven by air pulses delivered to a molded cassette through a plastic membrane. The cassette contains all components of a previously complex tubing set, except for the lines to the patient and short delivery lines from the dialysate containers. The air pulses are controlled by continually analyzing the pressure changes in the air delivered to the diaphragm, processing them through a computer, and making continual corrections as a result. This resulting system is able to accurately measure the fluid delivered, but is unable to provide a fixed steadiness of flow rate. In contrast to peritoneal dialysis systems, systems such as photopheresis systems, which involve continuous blood cell separation, require both a very steady flow rate, as well as the ability to control the fluid flow rate.

It is therefore an object of the present invention to provide a pump that achieves an accurate, steady flow rate, and which may be used to facilitate blood cell separation during photopheresis treatment of diseases.

These and other objects and advantages of the invention will become more fully apparent from the description and claims which follow or may be learned by the practice of the invention.

SUMMARY OF THE INVENTION

The present invention is directed to an apparatus for pumping fluid at a steady rate. A first drive chamber having a movable outer surface, and a second drive chamber having a movable outer surface are provided. The apparatus further includes a block having a plurality of internal passages including a first passage for receiving the fluid into the block and a second passage for discharging the fluid from the block at the steady rate. The block has first and second internal chambers which are in fluid connection with the first and second passages. The first internal chamber has a first flexible surface for mating with the movable outer surface of the first drive chamber, and the second internal chamber has a second flexible surface for mating with the movable outer surface of the second drive chamber. At least one actuator is provided for applying positive pressure to the first flexible surface while simultaneously applying negative pressure to the second flexible surface and for applying negative pressure to the first flexible surface while simultaneously applying positive pressure to the second flexible surface. The actuator is respectively coupled to the first and second flexible surfaces by the first and second drive chambers.

BRIEF DESCRIPTION OF THE DRAWINGS

In order that the manner in which the above-recited and other advantages and objects of the invention are obtained and can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

DETAILED DESCRIPTION OF THE INVENTION

Figure 1:
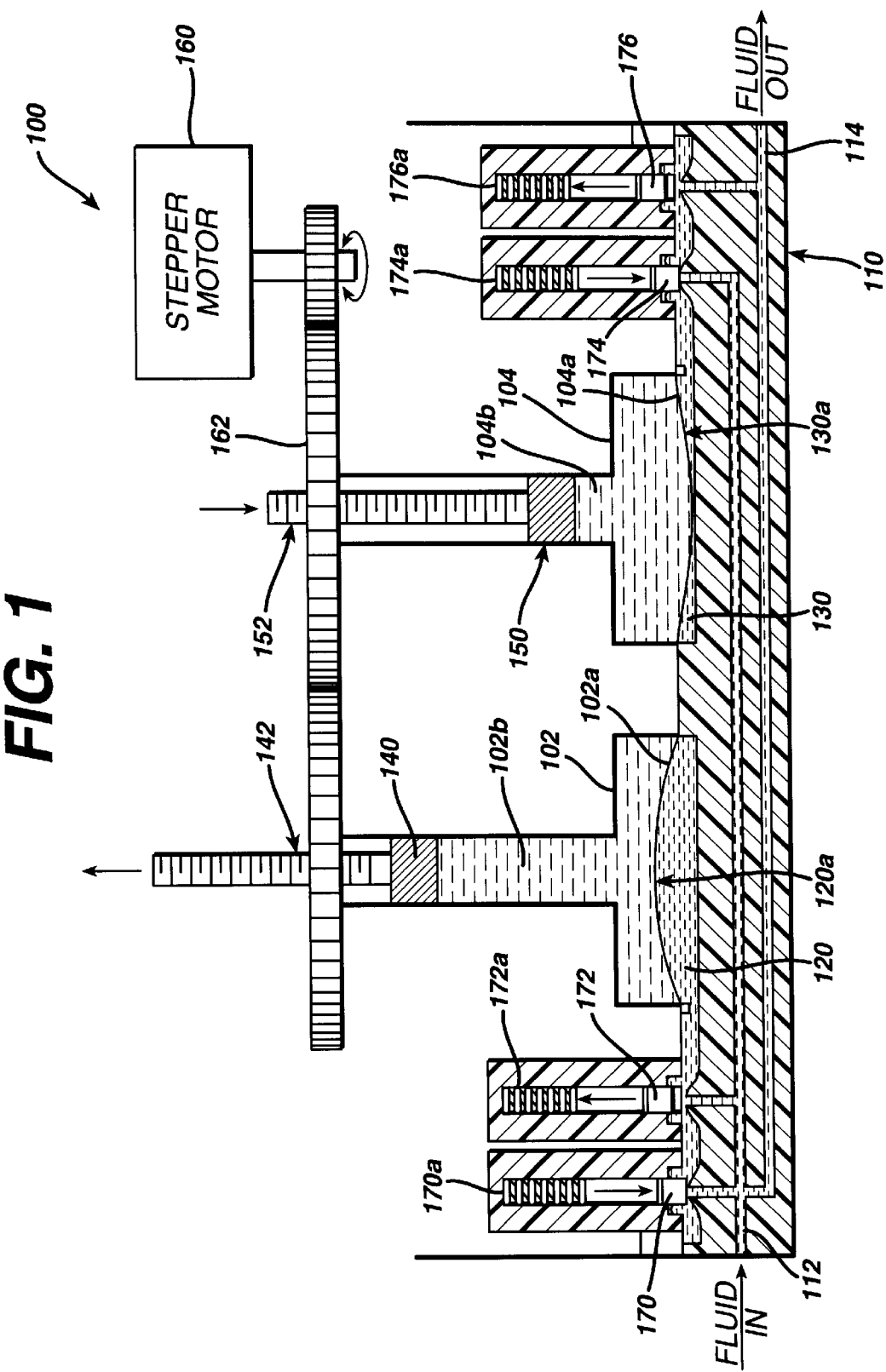
FIG. 1 is a cross-sectional diagram showing a system for pumping fluid at a steady rate, in accordance with a preferred embodiment of the present invention.

Referring now to FIG. 1, there is shown a cross-sectional diagram showing a system 100 for pumping fluid at a steady rate, in accordance with a preferred embodiment of the present invention. System 100 includes a first drive chamber 102 having a movable outer surface 102a, and a second drive chamber 104 having a movable outer surface 104a. Movable outer surfaces 102a and 104a are formed of a flexible material such as, for example, a flexible membrane. The first drive chamber 102 contains a fixed volume of drive fluid 102b, and the second drive chamber 104 contains a fixed volume of drive fluid 104b.

System 100 also includes a monolithic block 110 having a first passage 112 for receiving fluid into block 110. Block 110 also includes a second passage 114 for discharging fluid from block 110 at a steady rate. Block 110 has a first internal chamber 120 and a second internal chamber 130. Internal chambers 120 and 130 are coupled to the first passage 112 and the second passage 114 by valves 170, 172, 174 and 176. The first internal chamber 120 has a flexible surface 120a that mates with the movable outer surface 102a of the first drive chamber 102. Similarly, the second internal chamber 130 has a flexible surface 130a that mates with the movable outer surface 104a of the second drive chamber 104. Flexible surfaces 120a and 130a are preferably formed of a flexible membrane material. Flexible surface 120a is preferably sealed against movable outer surface 102a by mechanical force such that air is prevented from entering in between the surfaces 102a and 120a; similarly, flexible surface 130a is preferably sealed against movable outer surface 104a by mechanical force such that air is prevented from entering in between the surfaces 104a and 130a. In the preferred embodiment shown in FIG. 1, flexible surfaces 120a and 130a are collectively formed of a single continuous piece of flexible membrane material that covers the entire upper surface of block 110 and allows block 110 to be detached from the remaining components of blood pumping system 100 without leakage of fluids from block 110.

Referring still to FIG. 1, system 100 further includes a first piston 140 coupled to drive chamber 102, and a second piston 150 coupled to drive chamber 104. A first lead screw 142 is affixed to the first piston 140, and a second lead screw 152 is affixed to second piston 150. The first lead screw 142 and the second lead screw 152 are coupled to a motor 160 by a common helical drive gear 162. As motor 160 turns, the common helical gear drive 162 causes the first and second lead screws 142 and 152 (and pistons 140 and 150) to move vertically at equal speeds, but in opposite directions. Thus, as shown in FIG. 1, when lead screw 142 is causing piston 140 to move upwardly, lead screw 152 is simultaneously causing piston 150 to move downwardly. Similarly, when lead screw 142 is causing piston 140 to move downwardly, lead screw 152 is simultaneously causing piston 150 to move upwardly. Motor 160 is coupled to a pump controller (not shown).

When piston 140 is moved upwardly, the drive fluid 102b in drive chamber 102 causes the movable outer surface 102a to retract upwardly, thus applying a negative pressure to flexible surface 120a which causes flexible surface 120a to extend upwardly. As the flexible surface 120a extends upwardly, fluid from passage 112 is drawn into internal chamber 120. As mentioned above, at the same time that piston 140 moves upwardly, piston 150 moves downwardly. When piston 150 moves downwardly, the drive fluid 104b in drive chamber 104 causes the movable outer surface 104a to extend downwardly, thus applying a positive pressure against flexible surface 130a which causes flexible surface 130a to extent downwardly. As the flexible surface 130a extends downwardly, fluid from internal chamber 130 is expelled from block 110 through passage 114. After piston 140 has reached its uppermost position and piston 150 has simultaneously reached its lower-most position, motor 160 and gear drive 162 immediately cause pistons 140 and 150 to reverse directions such that piston 140 begins to move downwardly and piston 150 begins simultaneously to move upwardly. As piston 140 moves downwardly, the drive fluid 102b in drive chamber 102 causes the movable outer surface 102a to extend downwardly, thus applying a positive pressure to flexible surface 120a which causes flexible surface 120a to extend downwardly. As the flexible surface 120a extends downwardly, fluid from internal chamber 120 is expelled from block 110 through internal passage 114. When piston 150 moves upwardly (as mentioned above, this occurs when piston 140 moves downwardly), the drive fluid 104b in drive chamber 104 causes the movable outer surface 104a to retract upwardly, thus applying a negative pressure against flexible surface 130a which causes flexible surface 130a to extend upwardly. As the flexible surface 130a extends upwardly, fluid from passage 112 is drawn into internal chamber 130. After piston 140 has reached its lower-most position and piston 150 has simultaneously reached its upper-most position, motor 160 and gear drive 162 immediately cause pistons 140 and 150 to reverse directions again, and the process described above is repeated for another cycle. By continuously moving pistons 140 and 150 at equal speeds and in opposite directions, system 100 is able to pump fluid at a steady flow rate through block 110.

Referring still to FIG. 1, four valves 170, 172, 174 and 176 are used to control the flow of fluid through block 110 during the operation of system 100. Each of the valves 170, 172, 174 and 176 has an open position which allows fluid to pass through the valve, and a closed position which prevents any fluid from moving past the valve. Valve 170 is coupled to passage 114 and internal chamber 120, and controls movement of fluid between passage 114 and internal chamber 120; valve 172 is coupled to passage 112 and internal chamber 120, and controls movement of fluid between said passage 112 and internal chamber 120; valve 174 is coupled to passage 112 and internal chamber 130, and controls movement of fluid between passage 112 and internal chamber 130; and valve 176 is coupled to passage 114 and internal chamber 130, and controls movement of fluid between passage 114 and internal chamber 130. Solenoid actuators 170a, 172a, 174a and 176a are respectively coupled to valves 170, 172, 174 and 176, and are provided for moving the valves between their open and closed positions. Each of the solenoid actuators 170a, 172a, 174a and 176a are coupled to the pump controller (not shown). The controller can be a simple switching system that is triggered as pistons 140 and 150 reach the ends of their strokes in order to reverse the direction of motor 160 and the positions of valves 170, 172, 174 and 176.

In the preferred embodiment, the pump controller maintains valve 172 in its open position when valve 174 is in its closed position; the controller maintains valve 172 in its closed position when valve 174 is in its open position; the controller maintains valve 170 in its open position when valve 176 is in its closed position; and the controller maintains valve 170 in its closed position when valve 176 is in its open position. By controlling the operation of the valves 170, 172, 174 and 176 in this manner, the present invention insures that, at any given moment in time, fluid from passage 112 is being drawn into one and only one of the internal chambers 120 and 130 and that, at any given moment in time, fluid is being expelled (through passage 114) from one and only one of the internal chambers 120 and 130. Also in the preferred embodiment, the controller (which is coupled to motor 160) functions to cause surface 102a of drive chamber 102 to apply positive pressure to flexible surface 120a only hen valves 172 and 176 are in their closed positions and valves 170 and 174 are in their open positions; the controller functions to cause surface 102a of drive chamber 102 to apply negative pressure to flexible surface 120a only when valves 172 and 176 are in their open positions and valves 170 and 174 are in their closed positions, the controller functions to cause surface 104a of drive chamber 104 to apply negative pressure to flexible surface 130a only when valves 172 and 176 are in their closed positions and valves 170 and 174 are in their open positions; and the controller functions to cause surface 104a of drive chamber 104 to apply positive pressure to flexible surface 130a only when valves 172 and 176 are in their open positions and valves 170 and 174 are in their closed positions.

Figure 2:
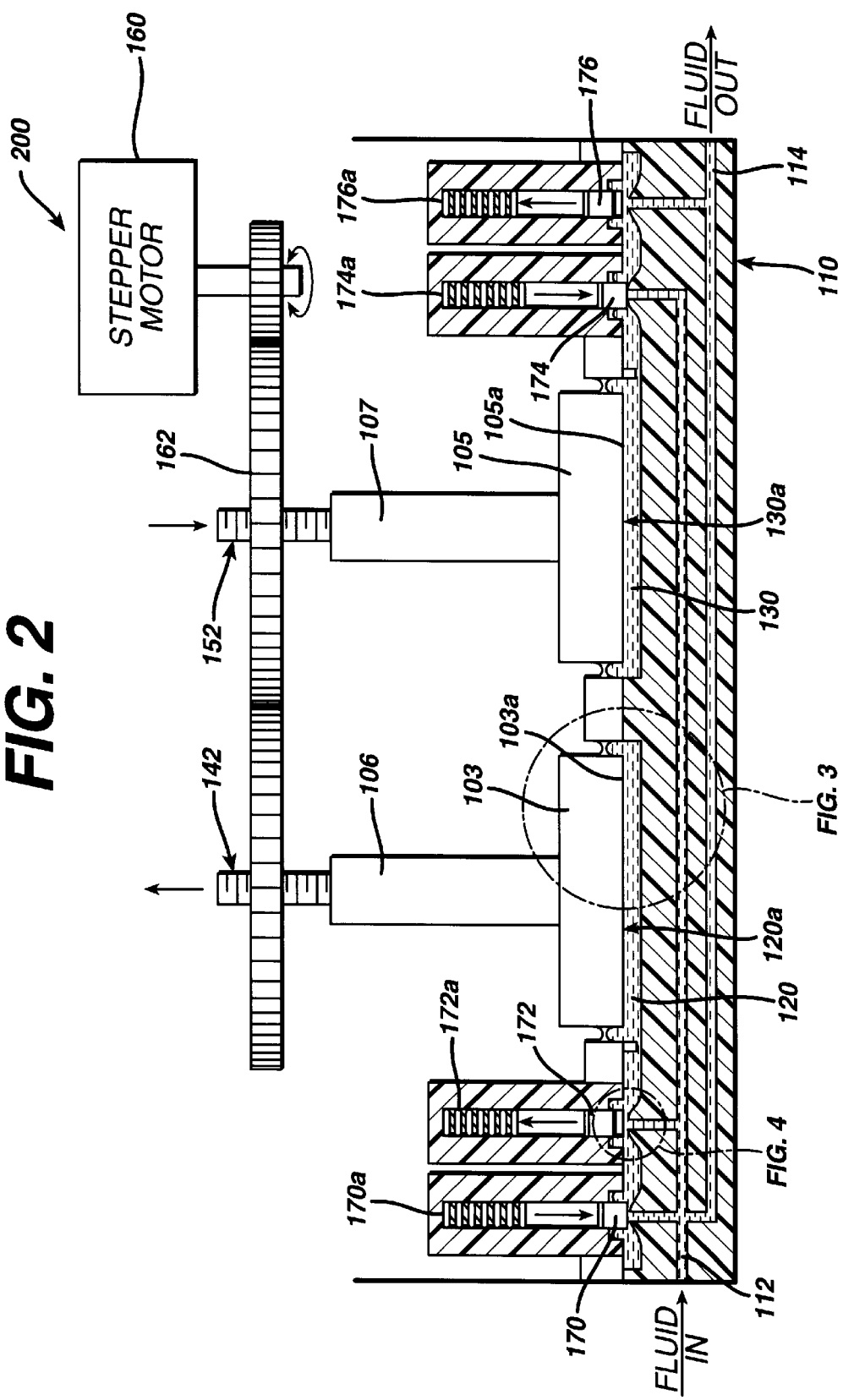
FIG. 2 is a cross-sectional diagram showing a system for pumping fluid at a steady rate, in accordance with an alternative preferred embodiment of the present invention.
Figure 3:
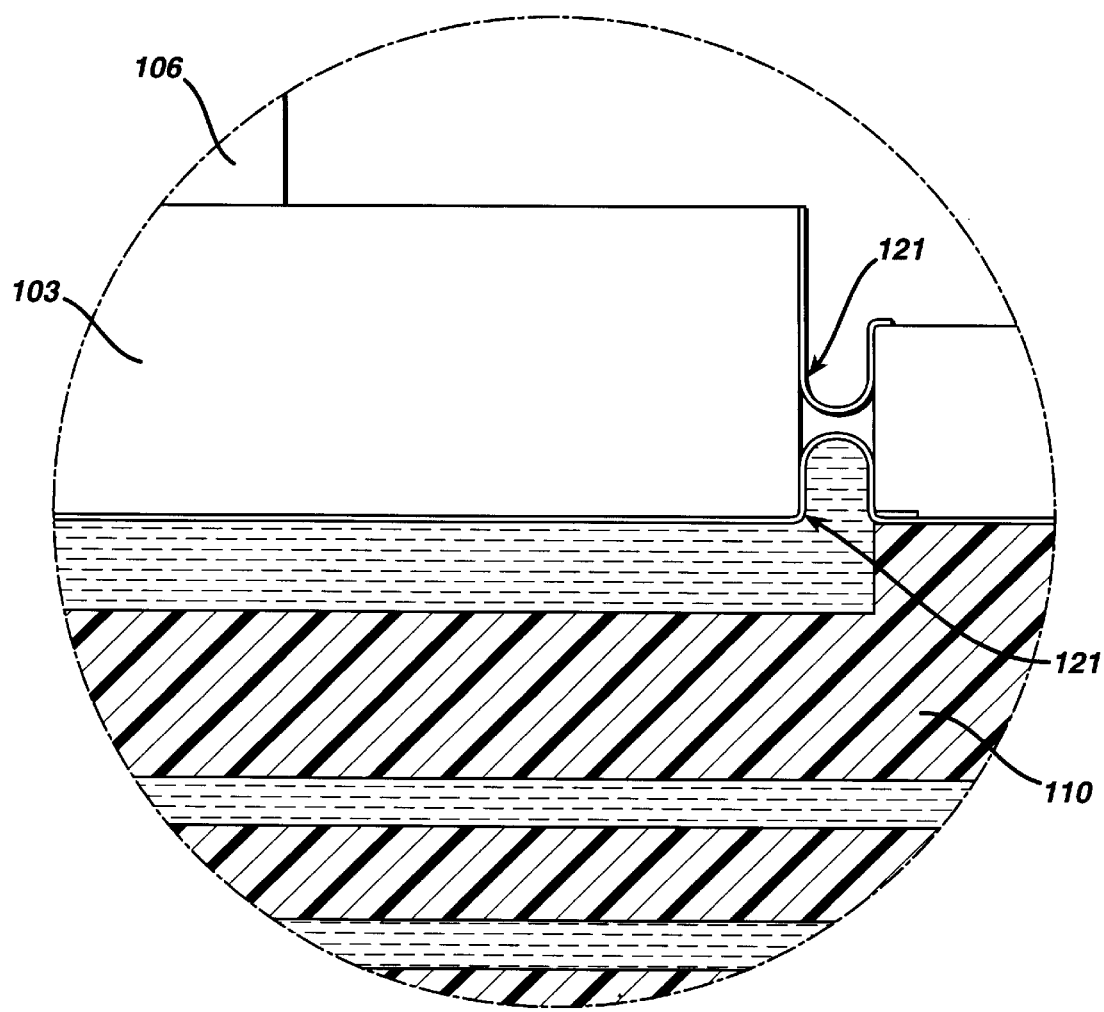
FIG. 3 is an enlarged view of a portion of the diagram shown in FIG. 2.
Figure 4:
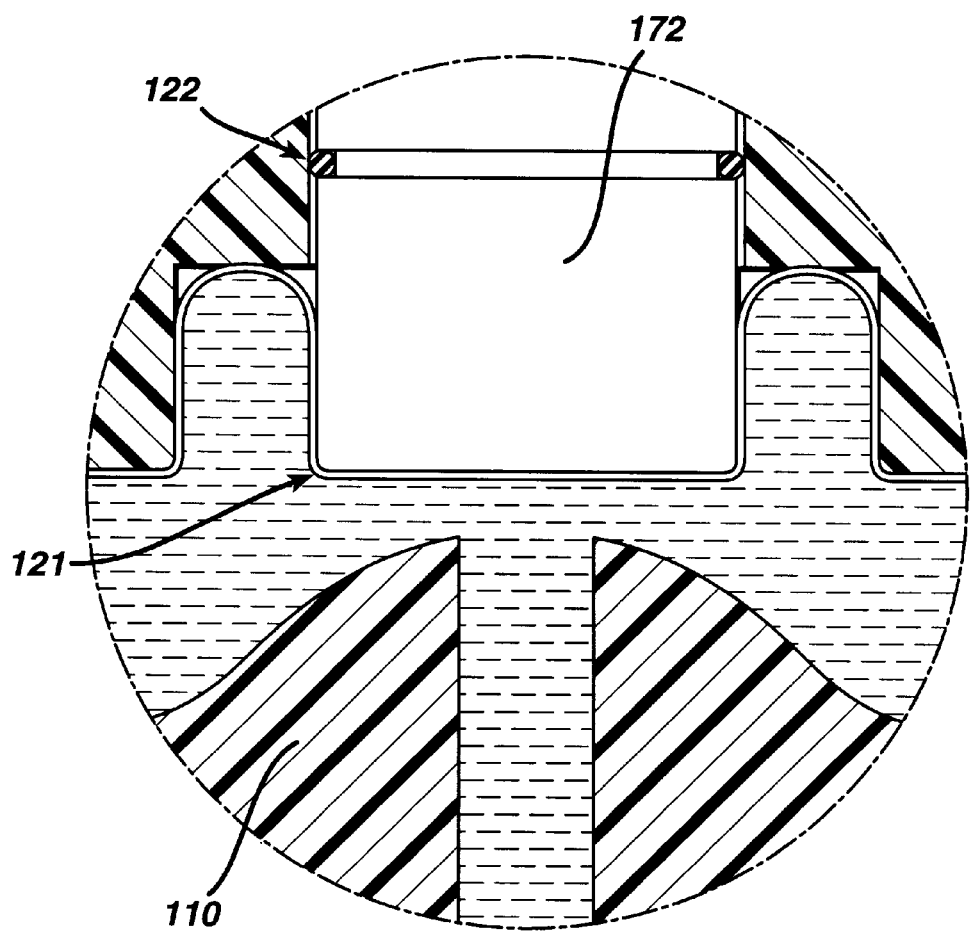
FIG. 4 is an enlarged view of a further portion of the diagram shown in FIG. 2.

Referring now to FIG. 2, there is shown a cross-sectional diagram of a system 200 for pumping fluid at a steady rate, in accordance with an alternative preferred embodiment of the present invention. Like numerals are used in FIG. 2 to identify components discussed previously above in connection with FIG. 1. System 200 functions substantially the same as system 100, except the drive chambers 102 and 104 and the pistons 140 and 150 from system 100 have been replaced in system 200 with rigid drive blocks 103 and 105 and drive members 106 and 107. Rigid drive block 103 is mechanically coupled to lead screw 142 by drive member 106, and rigid drive block 105 is mechanically coupled to lead screw 152 by drive member 107. In contrast to system 100 wherein drive chamber 102 had a movable outer surface 102a that was flexible, drive block 103 in system 200 includes a movable outer surface 103a which is rigid. Similarly, drive block 105 in system 200 includes a movable outer surface 105a which is rigid. Movable outer surfaces 103a and 105a of drive blocks 103 and 105 are preferably bonded to surfaces 120a and 130a, respectively. As shown in FIG. 3, rolling diaphragms 121 are preferably used to seal blocks 103 and 105 to block 110. These rolling diaphragms 121 function to seal blocks 103 and 105 to block 110 while, at the same time, allowing the blocks 103 and 105 to move in relation to block 110. As illustrated in FIG. 4, each valve 170, 172, 174, 176 is similarly sealed to block 110 by rolling diaphragms 121 and O-rings 122. The rolling diaphragms 121 and O-rings 122 illustrated in FIG. 4 function to seal the valves 170, 172, 174, 176 to block 110 while, at the same time, allowing the valves to move in relation to block 110. In a preferred embodiment of system 200, the rolling diaphragms 121 and the flexible surfaces 120a and 130a are collectively formed of a single continuous piece of flexible membrane material that covers the entire upper surface of block 110 and allows block 110 to be detached from the remaining components of system 200 without leakage of fluids from block 110.

Figure 5:
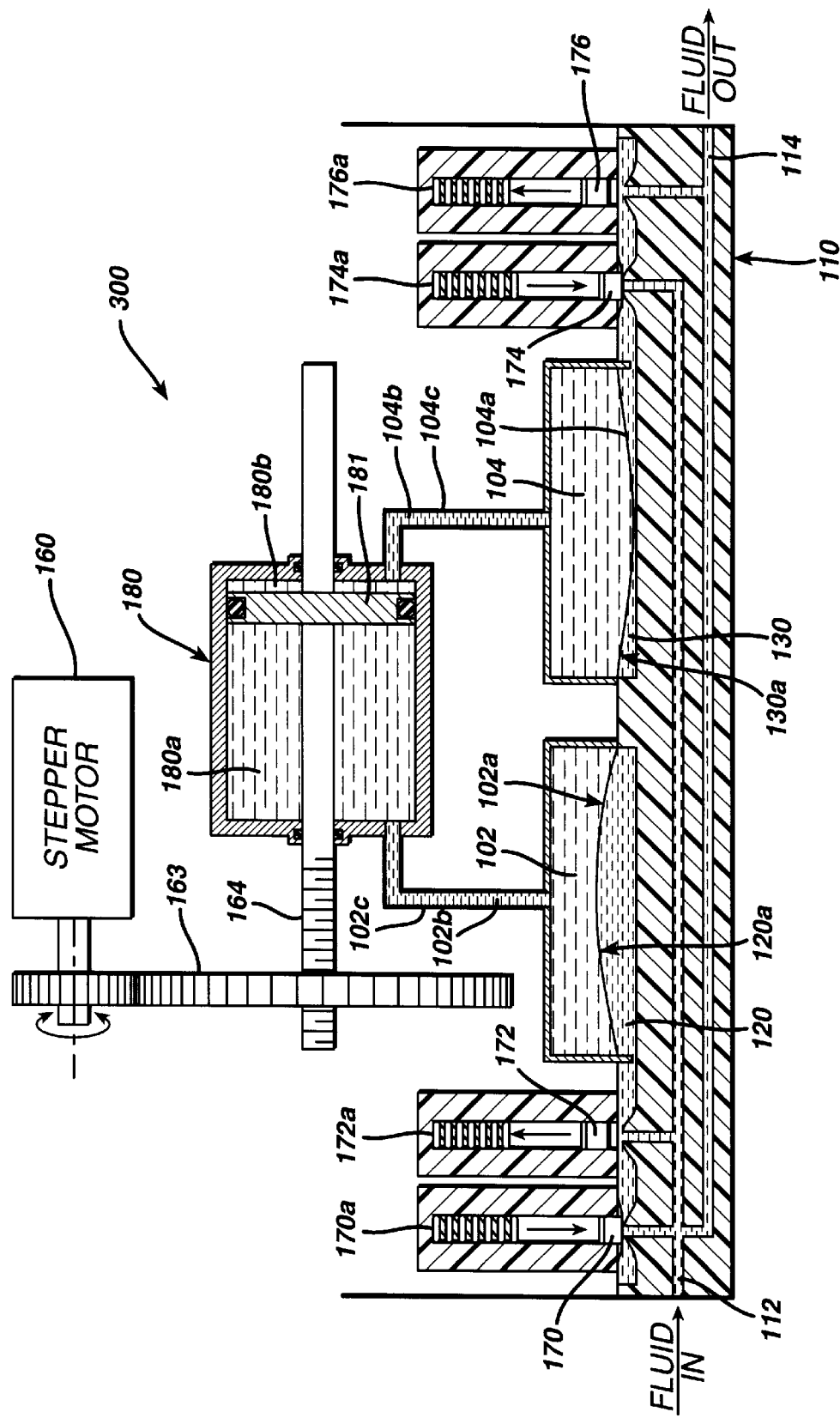
FIG. 5 is a cross-sectional diagram showing a system for pumping fluid at a steady rate, in accordance with a still further preferred embodiment of the present invention.

Referring now to FIG. 5, there is shown a cross-sectional diagram of a system 300 for pumping fluid at a steady rate, in accordance with an alternative preferred embodiment of the present invention. Like numerals are used in FIG. 5 to identify components discussed previously above in connection with FIG. 1. System 300 functions substantially the same as system 100, except the screws 142, 152 and 162 and the pistons 140 and 150 from system 100 have been replaced in system 300 with drive screws 163 and 164 and cylinder 180. Cylinder 180 includes a movable wall 181 which separates the interior of cylinder 180 into two separate compartments 180a and 180b. Compartment 180a is coupled to drive chamber 102 by fluid conduit 102c, and compartment 180b is coupled to drive chamber 104 by fluid conduit 104c. A fixed volume of drive fluid 102b occupies drive chamber 102, fluid conduit 102c and compartment 180a during operation of system 300. Similarly, a fixed volume of drive fluid 104b occupies drive chamber 104, fluid conduit 104c and compartment 180b during operation of system 300. Compartments 180a and 180b are isolated from each other by movable 181 such that drive fluid 102b in compartment 180a may not pass into compartment 180b and such that drive fluid 104b in compartment 180b may not pass into compartment 180a. In system 300, the individual volumes of compartments 180a and 180b are made to fluctuate in a cyclical fashion by translating movable wall 181 back and forth along the "x" axis. This cyclical movement of movable wall 181 causes the drive fluid 102b and 104b to either extend or retract the flexible surfaces 102a and 104a, thereby causing either positive or negative pressure to be applied cyclically and in equal but opposite directions to surfaces 120a and 130a, as described above in connection with FIG. 1. Drive screws 163 and 164 are coupled to motor 160, and are provided for translating movable wall 181 along the "x" axis.

Figure 6:
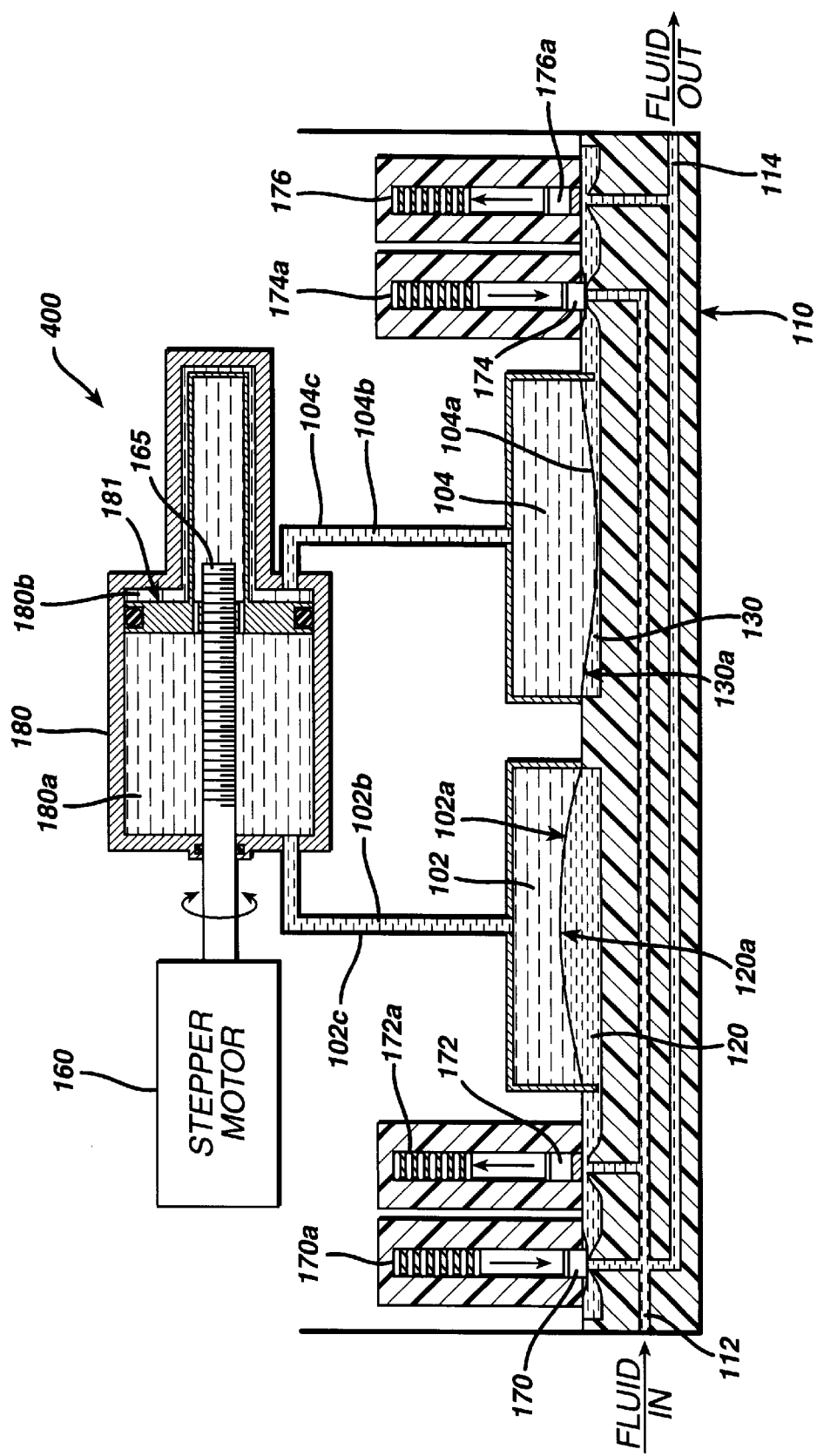
FIG. 6 is a cross-sectional diagram showing a system for pumping fluid at a steady rate, in accordance with a still further preferred embodiment of the present invention.

Referring now to FIG. 6, there is shown a cross-sectional diagram of a system 400 for pumping fluid at a steady rate, in accordance with an alternative preferred embodiment of the present invention. Like numerals are used in FIG. 6 to identify components discussed previously above in connection with FIGS. 1 and 5. System 400 functions substantially the same as system 300, except that screws 162 and 163 from system 300 have been replaced in system 400 with a single direct drive screw 165 which couples motor 160 directly to movable wall 181.

In a preferred embodiment of the present invention, the systems shown in FIGS. 1–6 are used to pump blood which is being either infused into or extracted from a patient. When the present invention is used for pumping blood, monolithic block 110 is made of a disposable material and is detachably secured to the remaining components of the blood pumping system. In this embodiment, a fresh sterile monolithic block 110 is attached to the remaining components of the blood pumping system at the beginning of a treatment session prior to pumping a patient's blood and, after the end of the treatment session, the used block 110 is detached from the remaining components of the blood pump and discarded.

Although in the preferred embodiment described above, the present invention is used to pump blood or other fluids that include blood constituents, it will be understood by those skilled in the art that the present invention may be used to pump other types of fluids. Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. An apparatus for pumping fluid at a steady rate comprising:

(A) a first drive chamber having a movable outer surface;

(B) a second drive chamber having a movable outer surface;

(C) a block having a plurality of internal passages including a first passage for receiving said fluid into said block and a second passage for discharging said fluid from said block at said steady rate, said block having first and second internal chambers in fluid connection with said first and second passages, said first internal chamber having a first flexible surface for mating with said movable outer surface of said first drive chamber, said second internal chamber having a second flexible surface for mating with said movable outer surface of said second drive chamber;

(D) at least one actuator for applying positive pressure to said first flexible surface while simultaneously applying negative pressure to said second flexible surface and for applying negative pressure to said first flexible surface while simultaneously applying positive pressure to said second flexible surface, said at least one actuator being respectively coupled to said first and second flexible surfaces by said first and second drive chambers.

2. The apparatus of claim 1, wherein said at least one actuator is in fluid communication with said first and second drive chambers.

3. The apparatus of claim 2, wherein said at least one actuator is in fluid communication with said movable outer surfaces of said first and second drive chambers.

4. The apparatus of claim 1, further comprising a first valve coupled to said first passage for controlling movement of said fluid between said first passage and said first internal chamber, a second valve coupled to said first passage for controlling movement of said fluid between said first passage and said second internal chamber, a third valve coupled to said second passage for controlling movement of said fluid between said second passage and said first internal chamber, and a fourth valve coupled to said second passage for controlling movement of said fluid between said second passage and said second internal chamber, wherein said first, second, third and fourth valves each have an open and a closed position.

5. The apparatus of claim 4, further comprising a controller for maintaining said first valve in said open position when said second valve is in said closed position, for maintaining said first valve in said closed position when said second valve is in said open position, for maintaining said third valve in said open position when said fourth valve is in said closed position, and for maintaining said third valve in said closed position when said fourth valve is in said open position.

6. The apparatus of claim 5, wherein said controller is coupled to said at least one actuator and functions to cause said at least one actuator to apply positive pressure to said first flexible surface only when said first and fourth valves are in said closed position and said second and third valves are in said open position, and wherein said controller further functions to cause said at least one actuator to apply negative pressure to said first flexible surface only when said first and fourth valves are in said open position and said second and third valves are in said closed position.

7. The apparatus of claim 6, wherein said controller functions to cause said at least one actuator to apply negative pressure to said second flexible surface only when said first and fourth valves are in said closed position and said second and third valves are in said open position, and wherein said controller further functions to cause said at least one actuator to apply positive pressure to said second flexible surface only when said first and fourth valves are in said open position and said second and third valves are in said closed position.

8. The apparatus of claim 5, further comprising first, second, third and fourth solenoids coupled to said controller for respectively actuating said first, second, third and fourth valves.

9. The apparatus of claim 1, wherein said at least one actuator is formed from a first piston coupled to said first drive chamber, a second piston coupled to said second drive chamber, said first piston having a first lead screw affixed thereto, said second piston having a second lead screw attached thereto, said first and second lead screws being coupled to a single motor by a common helical drive.

10. The apparatus of claim 9, wherein said movable outer surface of said first drive chamber and said movable outer surface of said second drive chamber are formed from rigid walls, said first and second flexible surfaces are formed from a flexible membrane, said movable outer surface of said first drive chamber being sealed to said first flexible surface, and said movable outer surface of said second drive chamber being sealed to said second flexible surface.

11. The apparatus of claim 9, wherein said movable outer surface of said first drive chamber and said movable outer surface of said second drive chamber are formed from a flexible membrane, and said first and second flexible surfaces are formed from a single piece of flexible membrane.

12. The apparatus of claim 11, wherein said first drive chamber has a first volume of drive fluid contained therein, and said second drive chamber has a second volume of drive fluid contained therein, said first and second volumes being fixed.

13. The apparatus of claim 1, further comprising a cylinder having first and second chambers separated by a movable wall, said first chamber of said cylinder being in fluid connection with said first drive chamber, said second chamber of said cylinder being in fluid connection with said second drive chamber, wherein said at least one actuator is formed of a motor, coupled to said movable wall, for varying a position of said movable wall within said cylinder.

14. The apparatus of claim 13, wherein said motor and said movable wall are coupled by at least one helical gear drive.

15. The apparatus of claim 13, wherein said movable outer surface of said first drive chamber and said movable outer surface of said second drive chamber are formed from a flexible membrane, and said first and second flexible surfaces are formed from a single piece of flexible membrane.

16. The apparatus of claim 15, wherein said first drive chamber, said first chamber of said cylinder and a first conduit connecting said first drive chamber and said first chamber of said cylinder collectively have a first volume of drive fluid contained therein, and said second drive chamber, said second chamber of said cylinder and a second conduit connecting said second drive chamber and said second chamber of said cylinder collectively have a second volume of drive fluid contained therein, said first and second volumes being fixed.

17. The apparatus of claim 1, wherein said fluid includes blood cells from a patient.

18. The apparatus of claim 17, wherein said block is adapted to be disposed of after use of said apparatus with said patient, and said first and second drive chambers and said at least one actuator are adapted to be reused with subsequent patients.

* * * * *